United States Patent
De

(10) Patent No.: US 9,885,708 B2
(45) Date of Patent: Feb. 6, 2018

(54) METHODS AND COMBINATIONS OF SIGNALING MARKERS FOR ASSESSMENT OF DISEASE STATES

(71) Applicant: DEEPATH MEDICAL INC., Palo Alto, CA (US)

(72) Inventor: Jita De, Palo Alto, CA (US)

(73) Assignee: DEEPATH MEDICAL INC., Palo Alto, CA (US)

( * ) Notice: Subject to any disclaimer, the term of this patent is extended or adjusted under 35 U.S.C. 154(b) by 0 days.

(21) Appl. No.: 14/647,414

(22) PCT Filed: Nov. 27, 2013

(86) PCT No.: PCT/US2013/072367
§ 371 (c)(1),
(2) Date: May 26, 2015

(87) PCT Pub. No.: WO2014/085679
PCT Pub. Date: Jun. 5, 2014

(65) Prior Publication Data
US 2015/0301032 A1 Oct. 22, 2015

Related U.S. Application Data

(60) Provisional application No. 61/797,024, filed on Nov. 27, 2012, provisional application No. 61/797,002, filed on Nov. 27, 2012, provisional application No. 61/797,006, filed on Nov. 27, 2012.

(51) Int. Cl.
*G01N 33/53* (2006.01)
*G01N 33/543* (2006.01)

(52) U.S. Cl.
CPC ... *G01N 33/5306* (2013.01); *G01N 33/54366* (2013.01)

(58) Field of Classification Search
None
See application file for complete search history.

(56) References Cited

U.S. PATENT DOCUMENTS

| | | | |
|---|---|---|---|
| 2003/0022253 A1* | 1/2003 | Moskal | G01N 33/5008 435/7.21 |
| 2003/0176409 A1* | 9/2003 | Offner | A61K 31/56 514/182 |
| 2014/0031308 A1* | 1/2014 | Diane | G01N 33/5005 514/43 |

OTHER PUBLICATIONS

Ornatsky et al. (J. Immunological Methods 2010 vol. 361, p. 1-20.*

* cited by examiner

*Primary Examiner* — Changhwa J Cheu
(74) *Attorney, Agent, or Firm* — Convergence Intellectual Property Law P.C.; Jonathan Garfinkel

(57) ABSTRACT

Methods for preparation of cells for analysis of biomarkers are disclosed. In one aspect, the method for preparation of cells for analysis of biomarkers includes contacting a sample that contains a population of cells with at least one modulating substance at a first temperature, thereby producing a modulated cell population; contacting the modulated cell population with at least one antibody that is directed to a cell surface biomarker at a second temperature that is lower than the first temperature, thereby producing an extracellularly stained cell population; and contacting the extracellularly stained cell population with one or more reagents that fixes and permeabilizes the cells, thereby producing a fixed and permeabilized cell population.

20 Claims, 13 Drawing Sheets

US 9,885,708 B2

METHODS AND COMBINATIONS OF SIGNALING MARKERS FOR ASSESSMENT OF DISEASE STATES

CROSS-REFERENCE TO RELATED APPLICATIONS

This application is a national stage entry under 35 U.S.C. 371 of PCT International Application PCT/US13/72367 filed on 27 Nov. 2013, which claims priority to U.S. Provisional Application Nos. 61/797,002, filed on Nov. 27, 2012, 61/797,006, filed on Nov. 27, 2012, and 61/797,024, filed on Nov. 27, 2012, all of which are incorporated herein by reference in their entireties.

FIELD OF THE INVENTION

The present disclosure relates to methods for sample preparation and quantitation of antigenic biomarkers on individual cells in a multiparametric cell analysis platform such as mass cytometry.

BACKGROUND

Comparison of primary neoplastic cells with control cells of same lineage has not been undertaken to show signaling nodes that are of particular significance due to high signaling activity in individual cell-types of myeloid neoplasms. Dynamic signaling states can be compromised when samples are cryopreserved. Thus, phospho-flow analysis performed on fresh samples can be theoretically more informative in identifying previously unidentified signaling aberrations than analysis performed on preserved samples.

Phospho-flow assays, which have typically been performed by fluorescent flow cytometry, have limitations due to the number of colors available per analysis tube. At best, fluorescent cytometry allows 18-20 markers to be evaluated simultaneously. However, overlap of fluorescence emission spectra requires set up of compensation settings that can often be time consuming. Further, tandem dyes can break down and emit signal at a different wavelength than expected, confounding results. Most commercial instruments are capable of analyzing less than 10 antibodies/tube. Thus, evaluating lineage markers and functional intracellular (IC) markers in a single tube assay has not been feasible. Multi-tube analysis can be time consuming and has precluded precise mapping of functional activity to cell-type, in particular rare cell-types (such as leukemic stem cells, dendritic cells, clonal T cells, etc.), some of which require at least 8-9 lineage- and cell type-determining surface markers (CD3, CD11c, CD14, CD19, CD33, CD34, CD45, CD117, CD123, etc.) for accurate identification based on presence or absence of markers. Fluorescent-labeled antibodies are generally more expensive and less stable than metal-tagged antibodies.

New methods are needed for analysis of large numbers of cell surface and intracellular markers simultaneously.

BRIEF SUMMARY OF THE INVENTION

In one aspect, a unique sample preparation method is provided for phos-flow analysis that incorporates a pre-fixation cooling step that lowers baseline signaling activity and results in a higher fold-change or distance between the induced and baseline state. A staining step for cell identification is performed prior to fixation. The method applies to modified samples that require surface staining for cell identification for applications that require use of live cells for further single cell analysis.

The method applies to cell lines, frozen or fresh mononuclear cells, fresh human samples, and any pathologic sample for biomedical research and to test novel inhibitors by cell-based pharmacoproteomic assays.

In another aspect, a sample preparation method is provided that allows fixation of a sample in its fresh state for baseline activity assessment. Simultaneous assessment of baseline signaling activities and cell identification is performed in the same experiment and applied for diagnostic and prognostic assays. The sample can be any human sample or solid tissue including blood, marrow, fine needle aspirates, and tissue biopsies comprised of a heterogeneous mixture of cells requiring cell-type identification. A strategy that combines a baseline evaluation by fresh sample fixation with surface staining performed post-fixation; and induced fold-change evaluation where surface staining is performed pre-fixation.

In another aspect, a novel combination of receptors and signaling markers is provided, including IL3R, IL7R, p-STAT5, p-STAT3, and p-p38 MAPK for identification of cells that have abnormally high signaling activities and based on their cell type can predict the cause of relapse, guide therapy, and prognosticate disease outcome. The sample can be any human sample or solid tissue including blood, marrow, fine needle aspirates, and tissue biopsies comprised of a heterogeneous mixture of cells requiring cell-type identification. This antibody panel applied in high throughput cytometry assays for prognostic and diagnostic evaluation and drug discovery in chronic myeloid leukemia, and other acute and chronic myeloproliferative leukemias, and Ph+ acute lymphoblastic leukemia.

In another aspect, data analysis methods are provided based on user selection of cell-types, ex vivo perturbations, functional readouts, etc. High dimensional plotting of select parameters generate patterns that allow interpretation of high throughput cytometry data and discover correlations such as between biochemical pathways and uncover underlying pathobiology. Cell type-specific proteomic profiles (mapping antigen expression profile to the identified cells) are provided that facilitate data interpretation through visualization of post-analysis data with simultaneous views showing cell proportions to demonstrate relative burden of disease. Quantitative data inclusive of cell fractions and expression levels of biomarkers allow comparison of datasets acquired from different time points to monitor therapy response. High dimensional plots based on selection of certain parameters that allow interpretation of high parameter datasets are provided.

DETAILED DESCRIPTION

Figure 1:
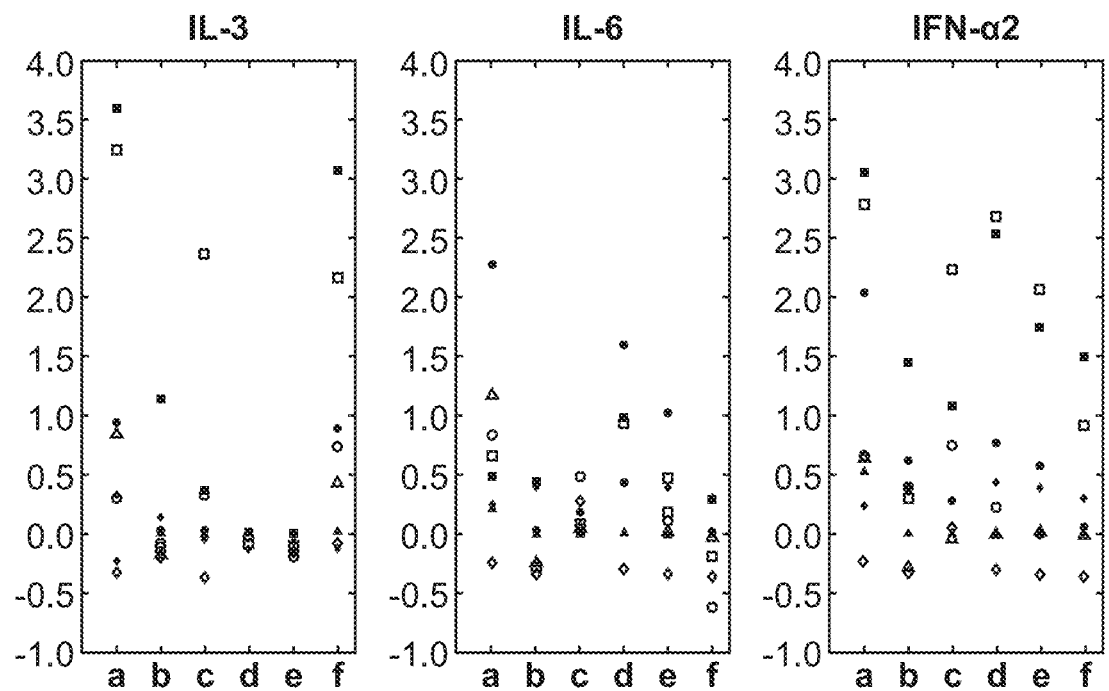
FIG. 1 illustrates cytokine-induced fold-change above baseline when using the pre-fixation staining method in chronic-phase CML patient compared to control for selected cell-types (a. monocytes, b. neutrophils, c. B cells, d. CD4 T cells, e. CD8 T cells, f. Basophils) and intracellular (IC) protein readouts (square: p-STAT5, circle: p-STAT3, triangle: p-p38 MAPK, and diamond: total IKB kinase). By this method, in myeloid lineage cells (neutrophils, monocytes, and basophils), all patient cells have higher IL3- and IFNα2-induced p-STAT5 compared to normal counterparts. In monocytes and CD4 T cells, IL6-induced p-STAT3 compared to normal control cells. These fold-change are less delineated in post-fixation staining method, in part due to high baseline activities in the latter method.
Figure 1:
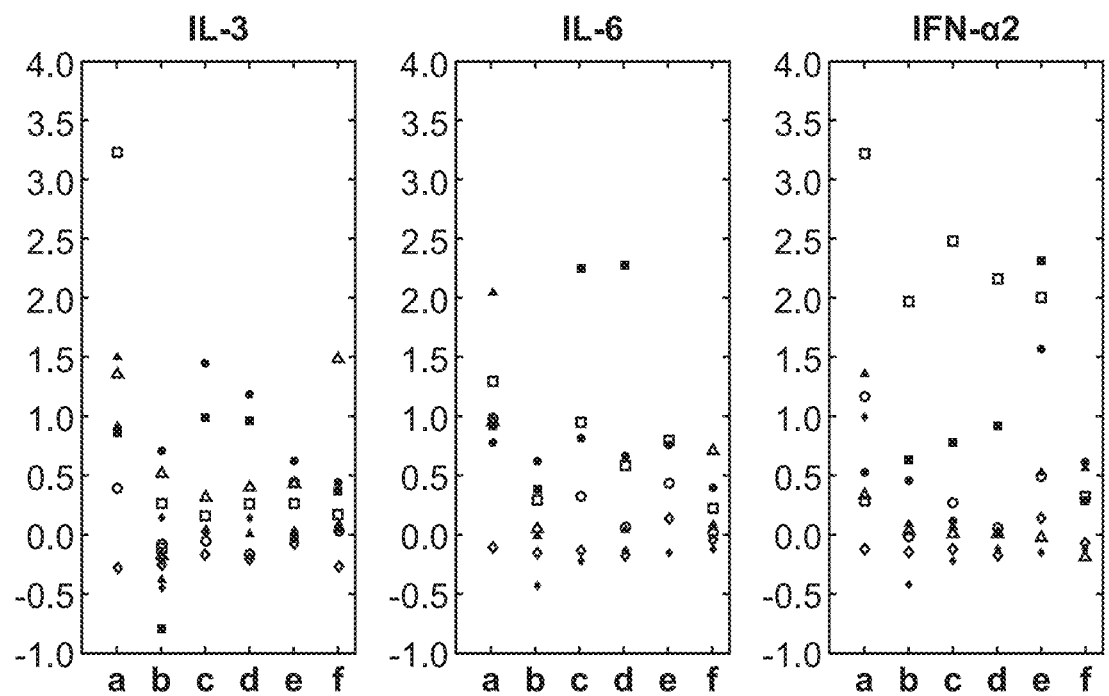

Methods and novel combinations of antibodies are provided for simultaneous quantitation of antigenic biomarkers in individual cells. Cell-based assays are provided to measure early, residual, or relapsed disease states for therapy guidance and to assess the biologic effects of ex vivo perturbations. Proteomic profiles that emerged from the data provided herein allow for prediction of therapeutic outcome and therapy responsiveness. Deregulated protein expression and activation profiles in certain cell-types (effector and memory T cells, neoplastic clones, NK cells, dendritic cells, etc.) of heterogeneous cellular mixtures (blood, bone marrow, mononuclear cells, body fluids, fine needle aspirates, core needle biopsy, etc.) are determined by a next-generation highly multiparametric cell analysis platform such as mass cytometry.

Using mass cytometry, a combination of markers was identified that is not routinely applied in diagnostics or for minimal residual disease (MRD) identification. A larger number of cell-identification markers used simultaneously than what is typically done allowed identification of rare stem/progenitors of both myeloid and lymphoid lineages. Routine MRD analysis does not incorporate signaling markers, essentially critical functional activity markers of neoplastic cells. The limitations of fluorescence flow, as described above, have precluded routine analysis of signaling activity. In addition, signaling states are highly dynamic and must be captured within a certain window of time after sample collection. Typically, overnight shipment of a blood or marrow sample, as is routine practice for most commercial laboratories, is not suited for analysis of signaling networks in fresh state. However, fixing the sample soon upon collection can be a way to circumvent this issue.

Expression levels of certain regulatory proteins within key pathways of convergence in target cell populations can predict disease states, unravel therapeutic targets and provide guidance for clinical decision-making. These cell-based "biomarkers" can be various receptors and/or downstream effectors with key biologic functions such as maturation, proliferation, DNA repair, apoptosis, etc., and may react to stimuli such as hypoxia, oxidative stress, and external growth factors. In disease states, many normal functions are affected and can be measured by altered protein levels or activation states.

As such, biomarker profiling of signaling pathways can generate response signatures associated with certain disease states for risk-stratification and outcome prediction, enabling personalized care and drug discovery. Innovative combinations of antibodies were designed for identification of cellular subsets of biomarkers including multilineage tumor clones and immunologic subsets, and quantitation of selected signaling biomarkers for cell type-specific biologic behavior was performed. Cell type-specific proteomic signatures associated with molecular relapse due to therapy non-adherence were identified, resulting in a cost-effective cell-based prognostic assay. Further, blood analysis allows for a non-invasive monitoring of therapy response and non-adherence.

Cytokine induction can enhance detection of signaling activity particularly for cells that are not rapidly multiplying and have relatively low baseline activity. In routine phospho-flow analysis, cytokine induction is followed by fixation of cells. However, fixation can compromise the integrity of antibody-binding sites and can render suboptimal staining results. In addition, distinction between baseline and induced activity can be masked by high baseline activity preserved by immediate fixation and readily detectable. A method where sample is allowed to cool while staining allows for both staining of live cells with preservation of antibody-binding sites, and simultaneous capture of induced signaling activity while lowering of baseline activity.

The protocol described here for cytokine-induced testing of signaling states includes a pre-fixation surface staining method. This method may be used for cell-specific signaling network analysis to assess the biologic effects of ex vivo perturbations that modify downstream proteins in a way in which their expression or activity level changes. Often changes in one key protein leads to a cascade of changes in downstream proteins, which may have important functional significance. Thus, multiple functional readouts are feasible and are informative in pharmacoproteomic assays.

Data visualization strategies are necessary to build predictive and explanatory models from high dimensional data derived from cytometry assays that are used to guide clinical management. The strategies allow selection of parameters based on variance in the dataset to generate correlative patterns associated with clinical situations such as medication non-adherence and may further predict effectiveness of targeted treatments for individual patients. Plots simultaneously showing expression of signaling markers in different signaling pathways within individual cell types can create cell type specific patterns, allowing identification of previously unknown correlations and cell-cell interactions. These are useful in communicating data to the medical and research community for optimal patient management.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates otherwise.

"Mass cytometry" refers to a single-cell multiparametric protein detection technology. Antibodies are tagged with isotopically pure rare earth elements, allowing simultaneous measurement of greater than 40 parameters while circumventing the issue of spectral overlap which is observed with fluorophores. The multi-atom metal tags are ionized, for example by passage through an argon plasma, and then analyzed by mass spectrometry. See, e.g., Bandura et al. (2009) *Analytical Chemistry* 81(16):6813-6822; Ornatsky et al. (2010) *Journal of Immunological Methods* 361(1-2):1-20; Bendall et al. (2011) *Science* 332(6030):687-696.

"SPADE" refers to "Spanning-tree Progression Analysis of Density-normalized Events." SPADE clusters phenotypically-similar cells into hierarchy that allow high-throughput, multidimensional analysis of heterogeneous samples. See, e.g., Qiu et al. (2011) Nat. Biotechnol. 29(10): 886-91.

"Phospho-flow" or "phos-flow" analysis refers to use of flow cytometry to analyze phosphorylated intracellular molecules at the single cell level, such as, for example, phosphorylated signaling proteins and cytokines.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact full-length antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies (as opposed to polyclonal antibodies) is highly specific, in the sense that they are directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

"Fv" is an antibody fragment that contains a complete antigen-recognition and binding site. In a two-chain Fv species, this region consists of a dimer of one heavy and one light chain variable domain in tight, non-covalent association. In a single-chain Fv species, one heavy and one light chain variable domain can be covalently linked by a flexible polypeptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site. A "Fab" fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

An epitope that "specifically binds" or "preferentially binds" (used interchangeably herein) to an antibody is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an epitope is an antibody that binds this epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the light chain or the variable region of the heavy chain, either alone or in combination.

"Complementarity determining region" (CDR) refers a relatively short amino acid sequence found in the variable regions of antibody molecules. The CDRs contain amino acid residues that determine the specificity of antibody molecules and make contact with a specific antigen.

Methods for Assessing Ex Vivo Perturbations of Cell Populations

Methods are provided for assessing effects of ex vivo perturbations on signaling pathways in cells of mixtures, such as heterogeneous biologic mixtures.

The disclosed methods may be used for analysis of alterations in regulatory proteins and their activation status due to external perturbations. For example, the method may be used in conjunction with phos-flow analysis of phosphorylation states.

In some embodiments, the method is a modification of standard phos-flow approach (e.g., where the cells are stained post-fixation and there is no cooling step prior to fixation). In contrast, the methods disclosed herein allow exaggeration of biologic effects due to external stimuli by cooling the sample, which quenches baseline (pre-stimulation) activity levels. Levels of certain biomarkers within modified signaling networks are determined in cell-types of interest. The data capture platform is a highly multiplexed cell analysis platform such as a mass cytometer.

A mixture of cells (e.g., a heterogeneous mixture of cells, such as blood, bone marrow, body fluids) is exposed to an exogenous stimulus (such as interleukins or hormones) that alters signaling, +/− an inhibitor that potentially alters cellular responses to modulators. The exogenous stimulus may include, but is not limited to, IL3, IL6, IFNα2, PMA, ionomycin, IFN-g, LPS, interleukins, SCF, FLT3L, GM-CSF, G-CSF, EPO, and/or TPO. The modified sample is then reacted with antibodies that bind to cell surface biomarkers, such as lineage-associated and other surface markers on ice. No stimuli (constitutive signaling) or drug inhibitor+ stimulator(s) may also be assessed. The sample is then fixed and permeabilized, and further reacted with antibodies towards intracellular markers.

The method may be conducted as follows:
1. The sample is exposed to one or more modulator(s) at a first temperature (e.g., 37° C.).
2. The modulated sample is then contacted with a panel of antibodies directed towards surface antigens at a second temperature that is lower than the first temperature (e.g., 0° C., for example, on ice).
3. The sample is subjected to fixation and permeabilization and is contacted with a panel of antibodies that bind intracellular antigens.
4. Data is captured on a multiparametric cell analysis platform and analyzed further using flow analysis and high-dimensional data analysis algorithms. Thus, comprehensive biomarker response profiles are generated for cell-specific effects of signaling modulators and test compounds.

In Example 1, lowering of baseline and more dramatic fold-change with the pre-fixation method disclosed herein is demonstrated, compared to the traditional post-fixation staining approach. The individual subpopulations are better delineated in the pre-fixation staining approach due to better preservation of surface epitopes.

Fixation of the cells may be performed with any reagent that is suitable for inactivation of enzymes, including but not limited to kinases, phosphatases, and proteases, in order to "fix" the in vivo state of phosphorytlation. In some embodiments, a paraformaldehyde-based fixative is used, such as Phosflow Lyse/Fix buffer, available from BD. In some embodiments, a formaldehyde-based fixative is used. Permeabilization of cells may be performed, for example, with an organic solvent, a detergent such as Triton X-100, or saponin. In some embodiments, fixation and permeabilization are performed simultaneously. In other embodiments, fixation and permeabilization are performed sequentially. In other embodiments, cells are not fixed but cooled and further analysis of a modified cell state is performed of live cells.

The methods described herein may be deployed with any suitable multiparametric cell analysis technique, including but not limited to, mass cytometry, multiplexed fluorescent flow cytometry, multiplexed immunohistochemistry, immunocytochemistry, and multiplexed qRT-PCR, e.g., any technique that is capable of use for quantification of single cell expression of a combination of analytes. Readouts) may include any post-translational modification due to a disease state (e.g., oncogenic disease state) or induced perturbed state, including, but not limited to, phosphorylation or acetylation.

In some embodiments, staining of a sample such as whole blood prior to fixation eliminates two wash steps which would have to be performed to remove fixative if fixation were performed prior to staining.

In some embodiments, some residual phosphatase activity during the cooling step may cause dephosphorylation, so the absolute level of phosphoproteins may be lower than observed in a post-fixation staining method.

Combinations of Cellular Markers for Multiparametric Analysis of Cell Populations Combinations of cellular markers and antibodies directed thereto are disclosed herein, which may be used, for example, for prognostic evaluation, outcome prediction, and therapy guidance in disease states. Combinations of antibodies disclosed herein may be used for simultaneous quantitation of antigenic biomarkers in individual cells.

Proteomic profiles that emerge from analysis of data generated for the combinations of biomarkers disclosed herein may allow for outcome prediction and therapy responsiveness. Deregulated protein expression and activation profiles in certain cell-types of cellular mixtures, such as heterogeneous cellular mixtures (e.g., blood, bone marrow, mononuclear cells, body fluids, fine needle aspirates, core needle biopsy, etc.) may be determined by highly multiparametric cell analysis platforms such as mass cytometry.

Combinations of antibodies are disclosed herein for identification of cellular subsets such as tumor sub-clones and immunologic subsets, and quantitation of selected biomarkers for cell-type specific biologic behavior. Biological features associated with unfavorable clinical factors may be identified leading to further research and development of cost-effective prognostic assays. For example, activated signaling networks in therapy-resistant subpopulations can guide further therapy by identifying survival pathways that can be more specifically targeted.

Antibodies directed to the following combination of biomarkers identified stem/progenitor cell subpopulations in the peripheral blood of a patient previously treated for chronic myelogenous leukemia who had been off therapy for 2 months: CD4-145Nd, CD20-147Sm, CD15-148Nd, CD7-149Sm, CD3-150Nd, CD123-151Eu, CD27-152Sm, CD45RA-153Eu, CD45-154Sm, CD19-156Gd, p-p38-157Gd, CD127-158Gd, CD11c-159Tb, CD14-160Gd, IgD-161Dy, p-ERK1/2-162Dy, IKBtot-163Dy, pSTAT3-164Dy, pS6 kinase-165Ho, CD16-166Er, CD38-167Er, CD24-168Er, CD117-169Tm, CD8a-170Er, CD66-171Yb, pSTAT5-172Yb, CD34-173Yb, HLA-DR-174Yb, CD56-175Lu, CD33-176Yb. In Example 2, a unique combination of markers, including CD19, CD34, CD117, and CD127/1L-7R identified therapy-refractory subpopulations with activated p-STAT5 and p-38 MAP kinase, which could predict relapse. This combination of markers allows for cell-specific biomarker assessment that is of prognostic and therapeutic relevance.

In various embodiments, combinations of antibodies directed to subsets of the biomarkers disclosed above may be used for analysis of various cell populations and samples, for analysis of disease states, determination of cell lineage and/or maturation, prediction of therapeutic outcomes, and/or analysis of therapeutic effectiveness.

The following examples are intended to illustrate, but not limit, the present disclosure.

EXAMPLES

Example 1

Materials and Methods

A fresh whole blood sample from a 54-year-old adult male patient with chronic-phase chronic myelogenous leukemia (CML) who presented with neutrophilic leukocytosis with a total WBC: 33.3 K/µl (PMN: 17.98 K/µl, Lymphocytes: 3.66 K/µl, Monocytes: 0.33 K/µl, Eosinophils: 0.67K/µl, Basophils: 4.0 K/µl, immature granulocytes: 6.3 K/µl, Blasts: 0.33 K/µl), Hb: 15.8 g/dL, Hct: 47.9%, and PLT: 536 K/µl was obtained from UCSF Helen Diller Family Comprehensive Cancer Center with informed consent. Cell-specific cytokine-induced effects in the leukemic v. normal state were compared. The sample was exposed to: IL3 (50 ng/ml), IL6 (50 ng/ml), IFNα2 10,000 IU/ml or no stimulus, for 15 min at 37° C.

Using the pre-fixation surface staining method, the modulated samples were then contacted with a cocktail of antibodies towards surface antigens for 15 minutes on ice, followed by fixation with Phosflow Lyse/Fix reagent (BD Biosciences, San Jose, Calif.) 10 minutes at 37° C., and washed 2× with "wash buffer" (PBS 0.1% BSA, 2 mM EDTA, 0.05% azide) by centrifugation at 500×g for 5 minutes.

Using post-fixation surface staining, a set of patient and healthy control samples was fixed immediately after the cytokine stimulation with BD Phosflow lyse/fix reagent for 10 min at 37° C. and washed 2× in wash buffer, followed by surface staining for 30 minutes at room temperature and washed 2× with wash buffer.

A panel of 27 metal-tagged antibodies was constructed using Maxpar polymers and lanthanide metals as per the manufacturer's conjugation protocol (DVS Sciences, CA). Surface staining was performed with the following antibodies against 1) lineage-determining antigens: CD8a-144Nd, CD4-145Nd, CD20-147Sm, CD16-Nd148, CD45-154Sm, CD11c-159Tb, CD14-160Gd, CD33-166Er, CD24-168Er, CD3-170Er, CD66-171Yb, CD56-175Lu; 2) activation- and maturation-associated antigens: CD27-152Sm, CD45RA-153Eu, IgD-161Dy, CD38-167Er, HLA-DR-174Yb, CD25-176Yb; and 3) cytokine receptors: IL3R/CD123-151Eu. After 2× wash in wash buffer, both sample sets (prepared by pre-fixation and post-fixation surface staining methods) were resuspended and permeabilized with 100% methanol, washed 2× in wash buffer, and labeled for analysis of select intracellular antigens using the following antibody conjugates: pp38 MAPK-157Gd, total IKB-163Dy, pSTAT3-164Dy, pSTAT1-169Tm, pSTAT5-172Yb, pPLCγ2-173Yb. After 1× wash, the samples were treated with DNA Iridium intercalator for a final concentration of 1:2000. The data were captured by inductive coupled time-of-flight cytometry (CyTOF) and analyzed by traditional gating tools and high dimensional data analysis algorithms including Spanning Tree Progression of Density Normalized Events (SPADE).

Results

Figure 2:
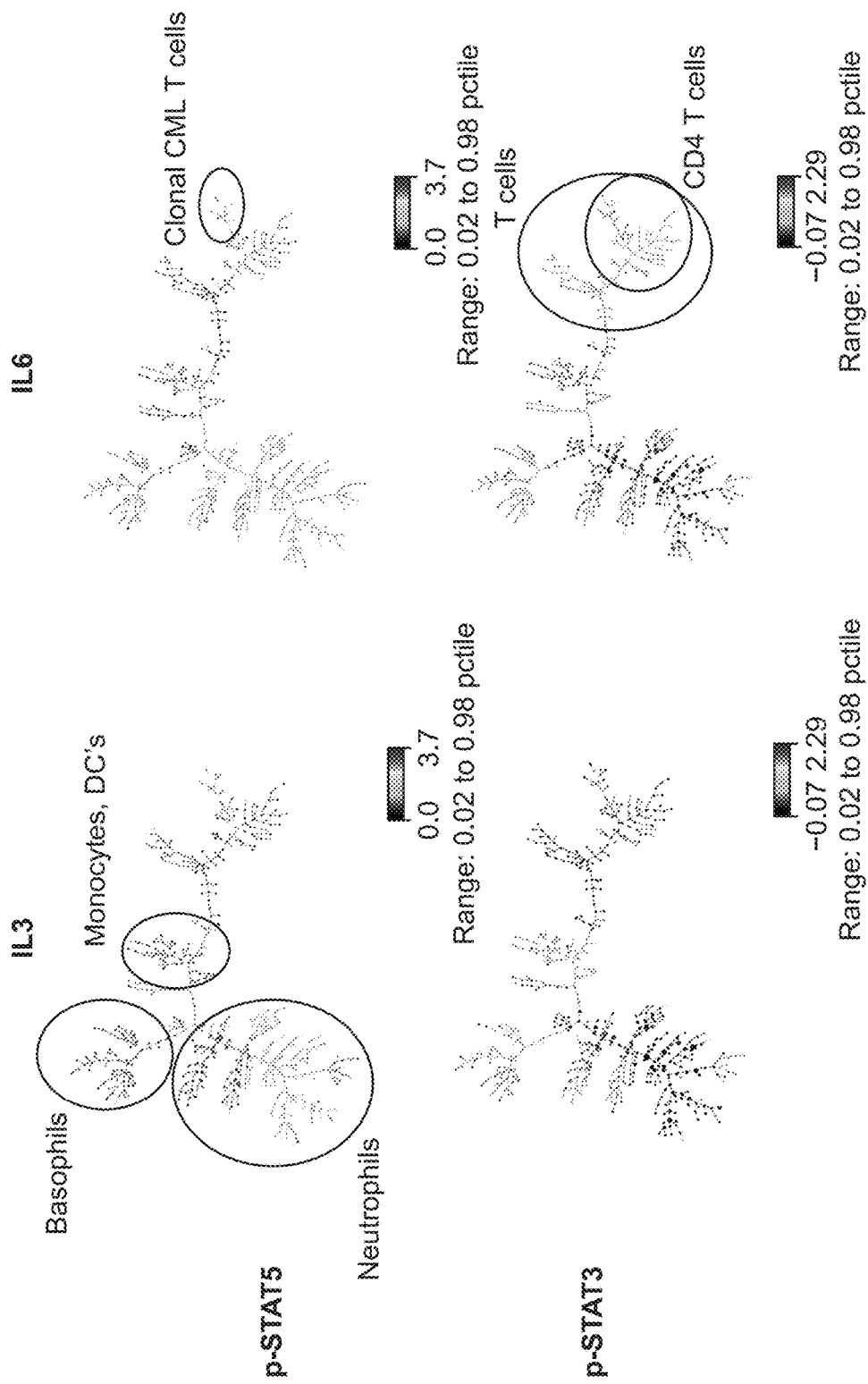
FIG. 2 depicts SPADE analysis performed for high dimensional clustering of cells to show differential induced STAT5 and STAT3 activities in the chronic phase CML blood sample. The analysis shows high induced IL3-STAT5 activity in cells arising from common myeloid progenitors (monocytes, myeloid DCs, neutrophils, basophils) and IL6-STAT3 activity in monocytes and CD4 T cells. Increased IL3-STAT3, STAT5 activity in CD33$^{hi}$ cells (basophils and monocytes) suggests correlation between STAT5 activity and CD33 expression. IL3, IL6-STAT5 activity is a possible marker of CML (BCR-ABL+) clonal T cells, while IL6-STAT3 activity is high in all CD4 T cells.

As compared to normal cell counterparts in the healthy control sample, CML cells in chronic phase had the following features:

A marked potentiated effect of IL3 on p-STAT5 in CML cells of myeloid lineage (neutrophils, monocytes, and basophils) was observed compared to majority of the lymphocytes in CML, rendering IL3-STAT5 a putative marker of neoplastic myeloid cells and possibly BCR-ABL positivity. IL6-STAT3 in CD4 T cells and monocytes likely represent immune response in CML (FIGS. 1 and 2).

Figure 3:
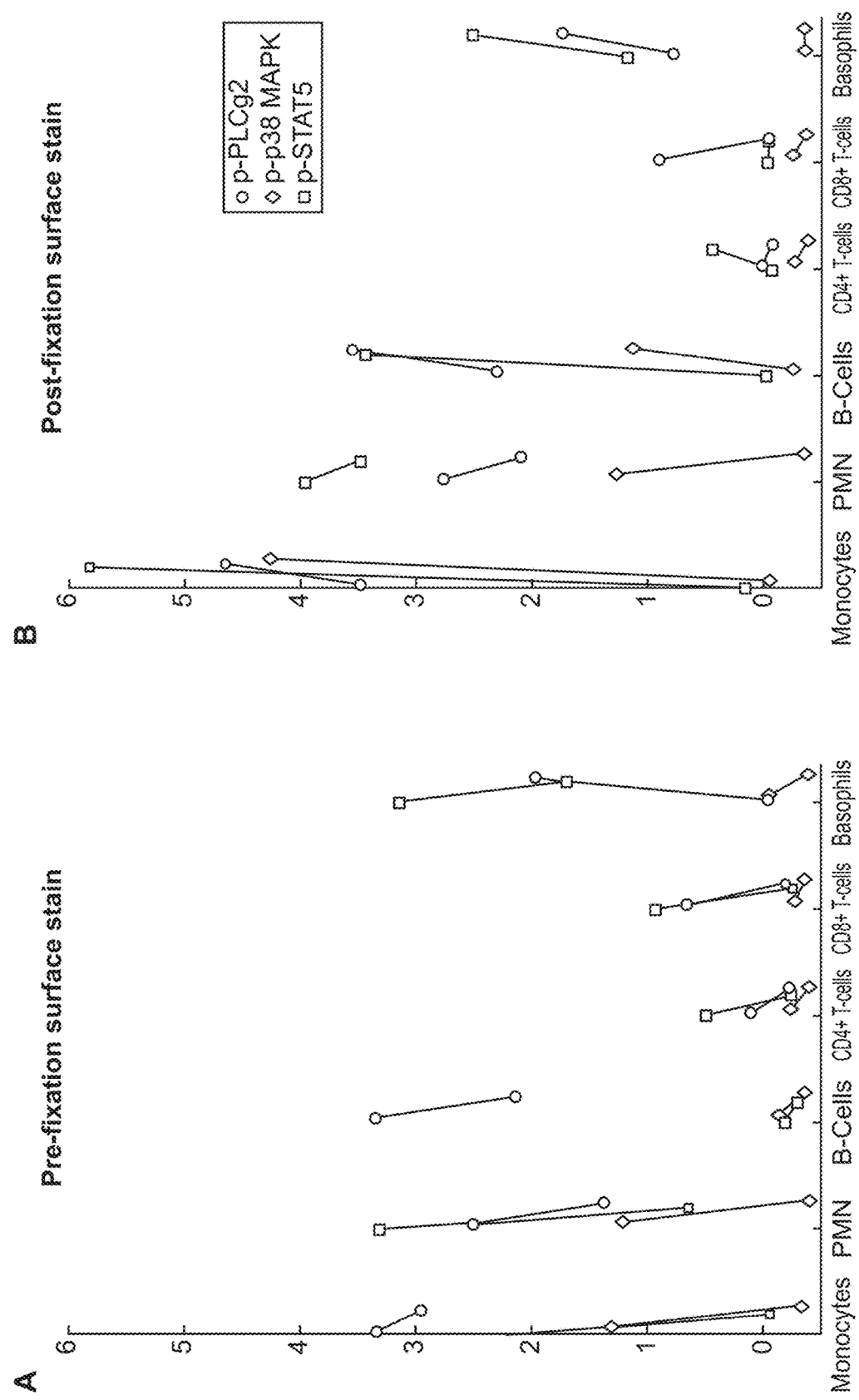
FIG. 3 illustrates baseline activities for selected cell-types (a. monocytes, b. neutrophils, c. B cells, d. CD4 T cells, e. CD8 T cells, f. Basophils) and IC protein readouts (p-STAT5, p-p38 MAPK, and p-PLCg2) in patient compared to control, comparing pre-fixation and post-fixation staining methods. Baseline activities are lower by pre-fixation method where cooling the sample (while staining for surface markers) causes enzyme inactivation thus lowering baseline activities with a prominent effect in patient cells compared to normal possibly due to more labile factors in the metabolically active patient cells.

Baseline signaling activity levels were more prominent in post-fix surface staining methods due to preservation of signaling activity through fixation. By pre-fixation surface staining, all patient cells had lower baseline than control, except pPLCγ2 readout in Basophils. Thus, pre-fixation surface staining caused lowering of baseline IC readouts in patient cells, suggestive of quenching of baseline phosphorylation possibly due to inactivation of enzymatic activity during cooling, with relative preservation of effects due cytokine induction. By post-fixation surface staining, CML monocytes, B-cells, and basophils have higher baseline than control, consistent with capture of high baseline activities in active state due to fixation prior to staining. CML PMNs had lower baseline compared to control (possibly due to reduction of STAT5 activity due to apoptosis). Slightly higher baseline p-STAT5 in CD4 T cells suggests admixed clonal CML T cells in the CD4 T cell subset (FIG. 3).

Figure 4:
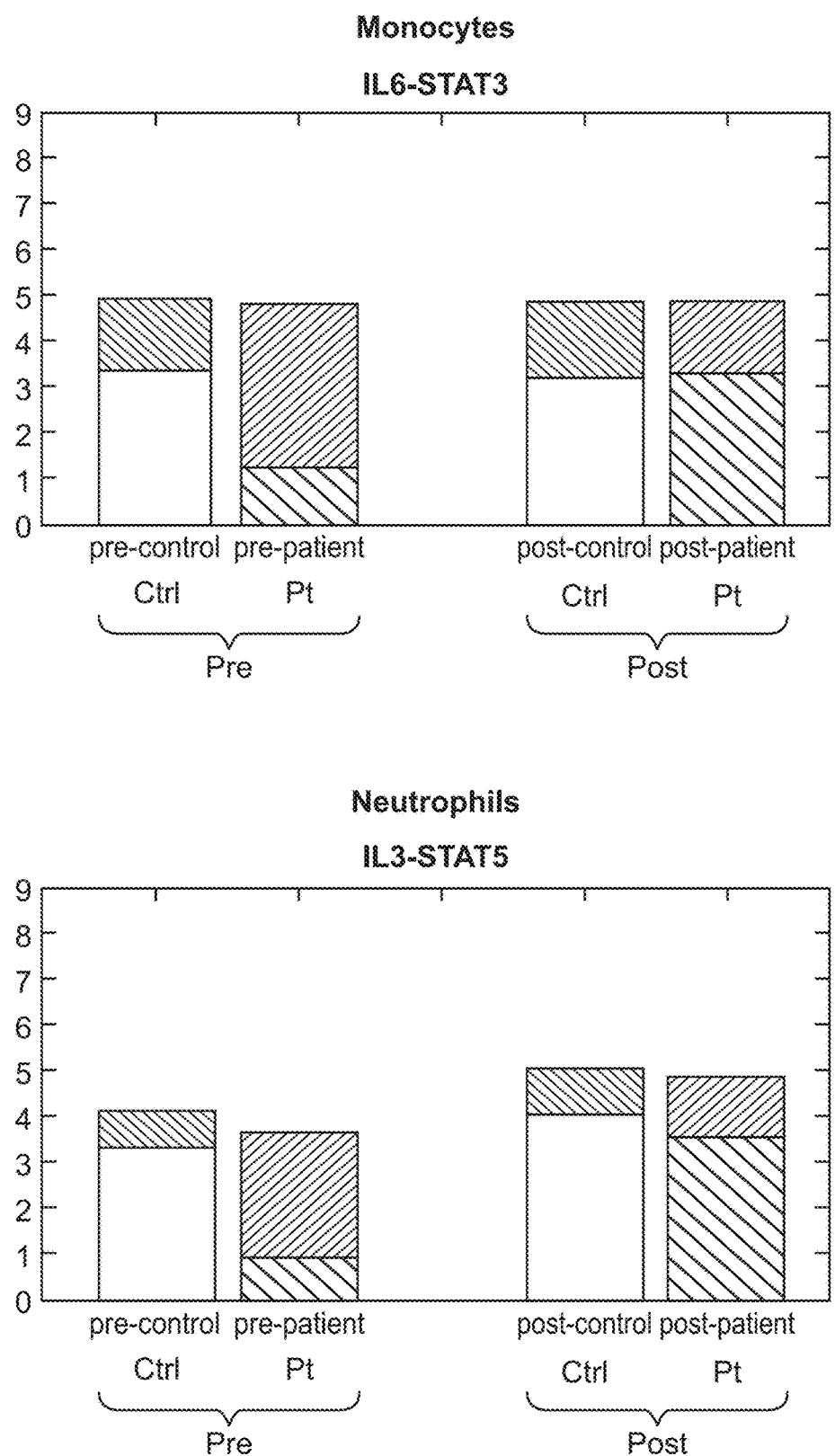
FIG. 4 illustrates lower baseline activities (represented by area below the dividing line in each bar) in patient cells compared to control cells, while the fold change (represented by area above the dividing line in each bar) is higher in patient cells compared to control cells using the pre-fixation method, while the post-fixation method failed to reveal a notable difference between induced change in the patient and healthy control cells.
Figure 7:
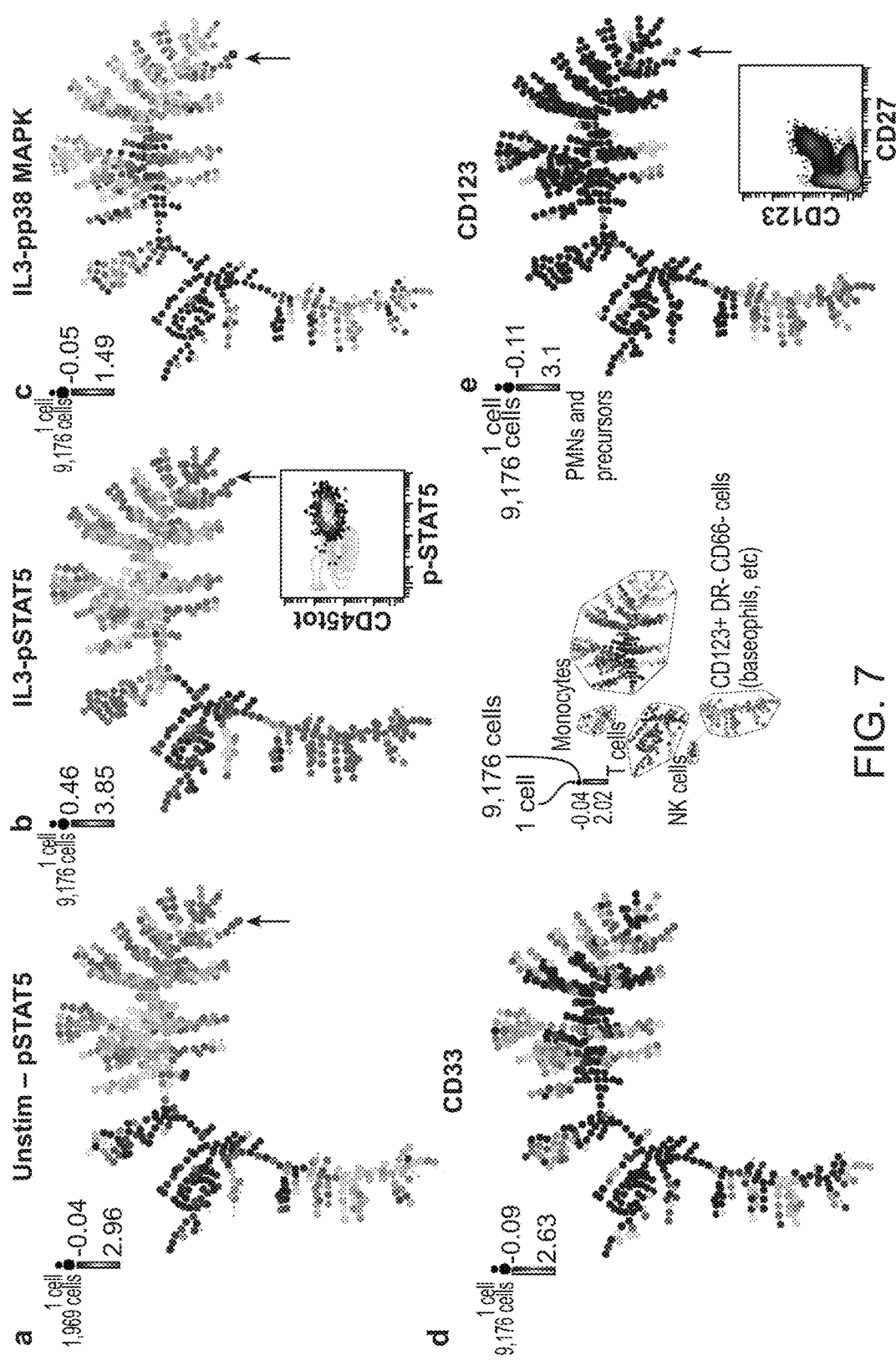
FIG. 7 shows SPADE analysis of all cells, arrow points to rare CD33+/IL3R+ cells that have high baseline and IL3-induced activity.

Fold-change ($log_{10}$ induced–$log_{10}$ basal) representing differential in the baseline and induced activity was higher in the pre-fixation surface staining method, possibly due to relative preservation of induced activity while quenching of baseline activity level due to enzyme inactivation in the cooling step. Elevated IL3-STAT5 in myeloid cells, and IL6-STAT3 in monocytes was observed in CML compared to healthy control cells when tested using the pre-fixation method as compared to the post-fixation method (FIG. 4). Thus, pre-fixation surface staining can unravel subtle post-translational modifications (which may be masked due to high baseline activity or poor preservation of low density lineage-determining antigen epitopes in the post-fixation staining method) induced due to ex vivo perturbations. Also, CD33+ subset was not as well distinguished in the post-fixation surface staining method due to non-specific and lowering intensity of CD33 signal (FIG. 7).

Differential cytokine-induced activity in CML cells based on stage of maturation with less differentiated (or multipotent progenitors) having lower growth factor responsiveness than more differentiated cells. Growth factor responsiveness could thus correlate with response to enzyme-targeted therapies that inhibit receptor-mediated signaling pathways.

Figure 5:
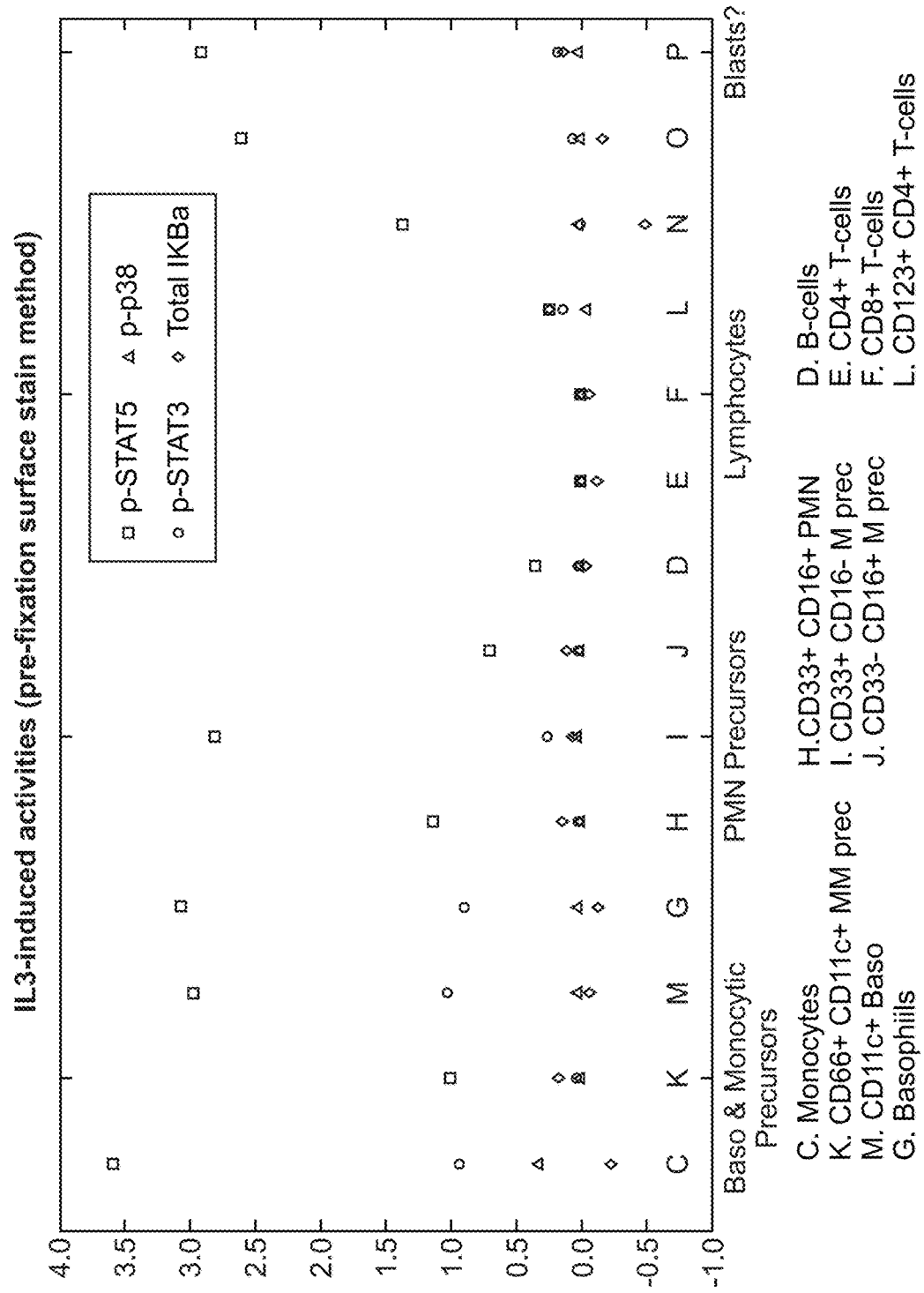
FIG. 5 illustrates cell type-specific activities in select IC protein readouts due to IL3 induction. The analysis is based on pre-fixation data due to better signal to noise ratio for CD33 antigen expression. IL3-induced p-STAT5 and p-STAT3 activities in CML clonal cells appear to be correlated with CD33 and possibly CD123 expression.

Delineation of $CD33^{hi}$ and $CD33^{lo}$ cells, performed by extracting cell subsets from the pre-fixation surface staining data set, demonstrated correlation between CD33 and IL3-STAT5 activity (FIG. 5).

Figure 6:
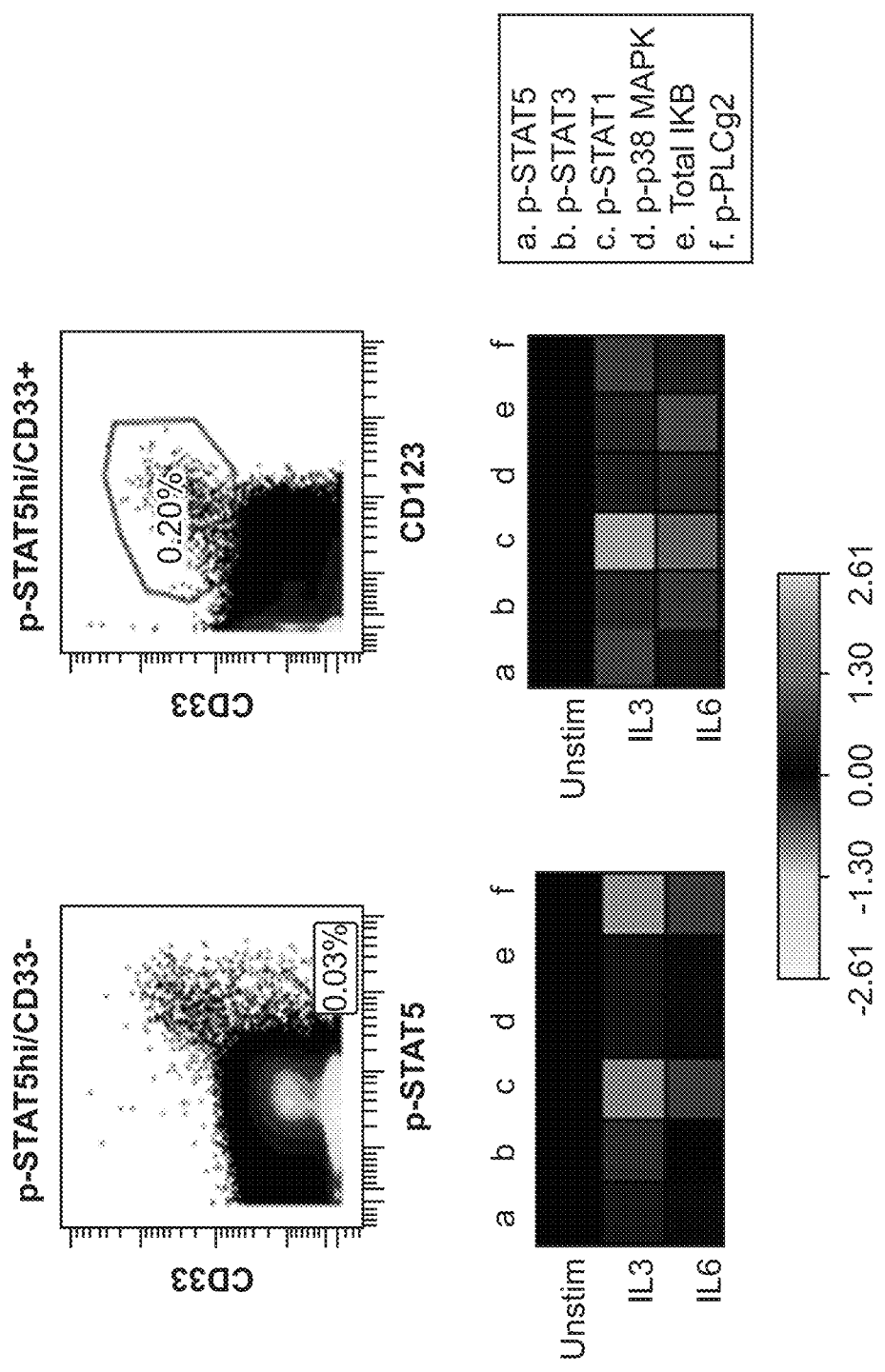
FIG. 6 illustrates differential induced STAT5 activities in CD33+ and CD33− cells gated by using p-STAT5 v. CD33, and CD33 v. CD123 bivariate plots. The CD33− undifferentiated CML stem/progenitor cells had lower IL3- and IL6-induced upregulation compared to more differentiated cells, possibly due to constitutive activity, with lower reliance on cytokines from the inflammatory milieu.

Lower IL3- and IL6-induced STAT5 responses in CD33−multipotent CML stem/progenitor cells (with high baseline p-STAT5 activity) (FIG. 6), suggests lower growth factor responsiveness (presumably due to BCR-ABL independent signaling activity) in treatment-refractory stem/progenitor cells. Thus cytokine-induced STAT5 activity could be a marker for TKI responsiveness useful for drug screening assays. Thus, drugs that increase the cytokine-response in stem/progenitor cells could be of therapeutic benefit in treated relapsed/refractory disease.

A minute CML myeloid progenitor subset (0.52%) with both high baseline and IL3-induced p38 MAPK and pSTAT5 activities (relative to more mature myeloid cells) correlated with CD27 and IL3R/CD123 expression (FIG. 7).

Figure 8:
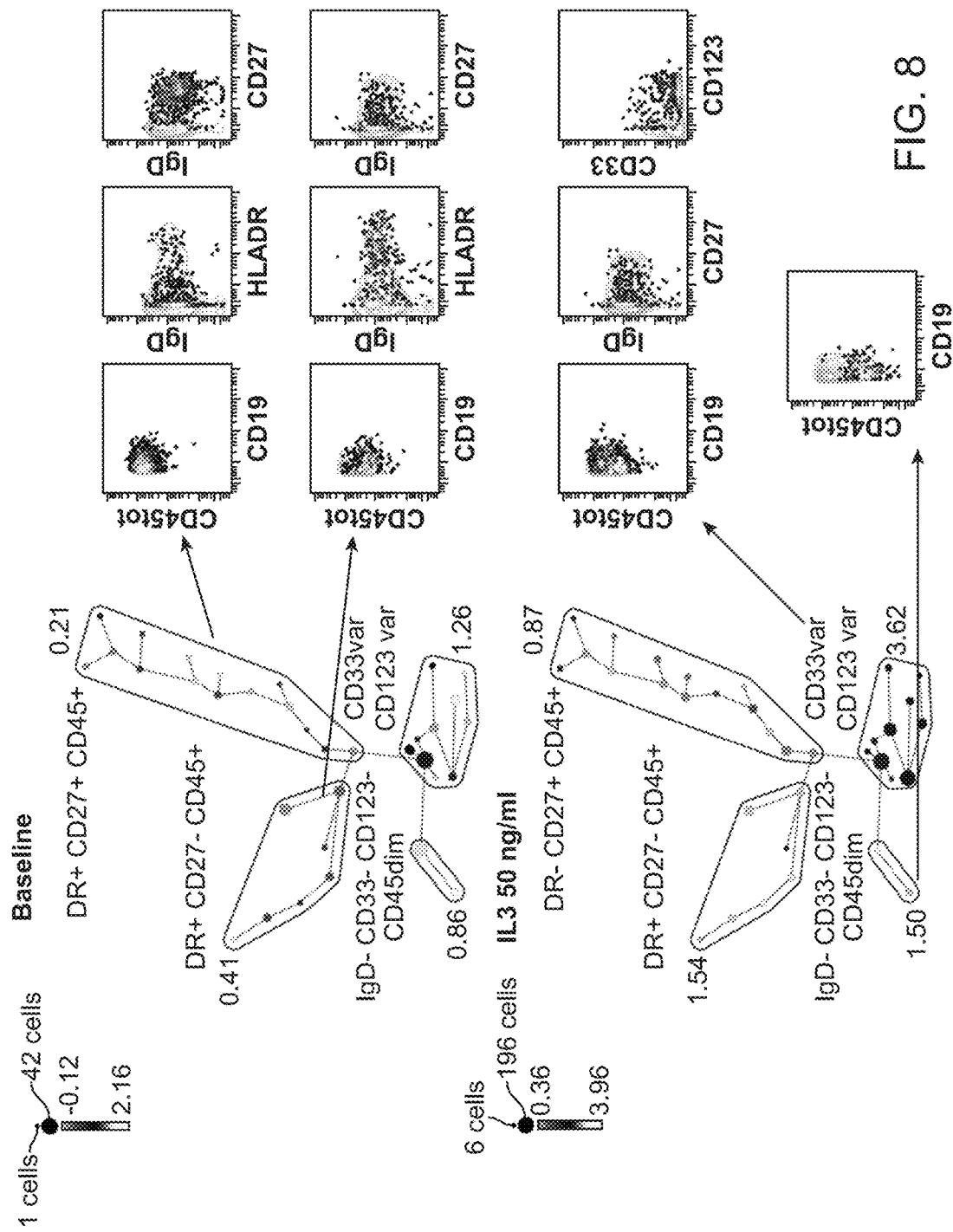
FIG. 8 shows SPADE analysis of CD19+ cell fraction, capturing cells co-expressing CD33 and/or IL3R cells with high baseline and IL3-induced p-STAT5 activity, suggesting admixed multipotent progenitor cells with high IL3-STAT5. More mature B cells lack significant p-STAT5 activity.
Figure 9:
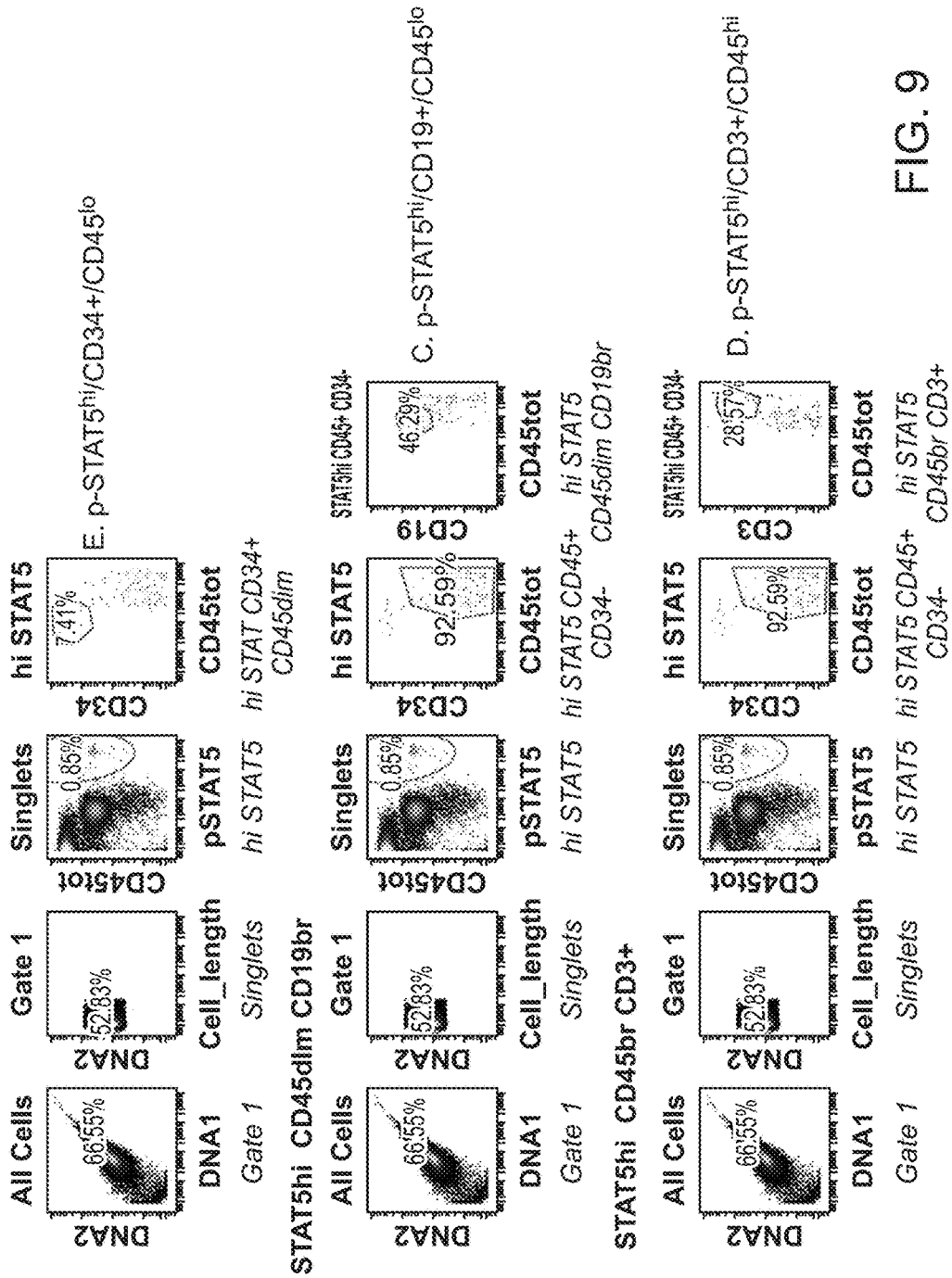
FIG. 9 shows identification of cells with high p-STAT5 activity in the patient sample with relapsed CML, and illustrates gating strategy used to identify the lineages of p-STAT5$^{hi}$ cells. Cells with high p-STAT5 activity levels were identified on CD45 v p-STAT5 bivariate plot. After identifying the CD34+ cells on CD34 v CD45 plot, CD19 v CD45 and CD3 v. CD45 plots were used for lineage identification of more differentiated CD34− or CD34$^{lo}$ cells. p-STAT5$^{hi}$ cells comprised of a mixture of CD19+/CD45$^{lo}$ and CD3+/CD45+ lymphoid progenitors and rare CD34+/CD45$^{lo}$ progenitor/stem cells.

CD19+ cell subsets had higher baseline and IL3- and IL6-induced STAT5 activity when co-expressing CD33 or CD123 myeloid markers, suggesting cells that are derived from the BCR-ABL (+) CML clone (FIG. 8). Similar cells are likely to be found in other Ph+ leukemia (including B-ALL and biphenotypic leukemia). Thus, CD19+/CD33+ and/or CD19+/CD123+ cells with activated STAT5 networks likely represent clonal BCR-ABL (+) cells in Ph+ leukemia, and CD19+ cells that are CD123+ or CD33+ and p-STAT5$^{hi}$ could be used for cell-based functional assays for detection of residual or relapsed disease.

Example 2

Materials and Methods

A fresh blood sample from a 74-year-old adult male patient previously on a BCR-ABL1 inhibitor for chronic-phase CML who presented with a normal total WBC: 7.9 K/μl (PMN: 3.43 K/μl, Lymphocytes: 3.41 K/μl, Monocytes: 0.82 K/μl, Eosinophils: K/μl, Basophils: K/μl, immature granulocytes: 6.3 K/μl), Hb: 14.1 g/dL, Hct: 40.7%, and PLT: 177 K/μl was obtained from UCSF Helen Diller Family Comprehensive Cancer Center with informed consent. Relapse due to non-adherence to therapy was suspected based on a BCR-ABL1/ABL1 p210 ratio of 0.285. The unmodified (baseline) sample was fixed in the BD Phosflow lyse/fix buffer 4 hours post-collection, washed with wash buffer, and stained with a panel of metal-conjugated antibodies. Surface staining was performed with antibodies against 1) lineage-determining antigens: CD4-145Nd, CD20-147Sm, CD15-148Nd, CD7-149Sm, CD3-150Nd, CD45-154Sm, CD19-156Gd, CD11c-159Tb, CD14-160Gd, CD16-166Er, CD24-168Er, CD117-169Tm, CD8a-170Er, CD66-171Yb, CD34-173Yb, CD56-175Lu, CD33-176Yb; 2) activation- and maturation-associated antigens: CD27-152Sm, CD45RA-153Eu, IgD-161Dy, CD38-167Er, HLA-DR-174Yb; and 3) cytokine receptors: IL3R/CD123-151Eu, IL7R/CD127-158Gd. The sample was permeabilized with 100% methanol −80° C. overnight, washed 2× in wash buffer, and labeled for analysis of select intracellular antigens using the following antibodies: pp38 MAP kinase-157Gd, pERK-162Dy, pSTAT3-164Dy, ppS6 kinase-165Ho; pSTAT5A-172Yb; and total IKB-163Dy for 30 minutes at RT. After 1× wash, the sample was treated with DNA Iridium nucleic-acid intercalator for a final concentration of 1:2000. The data were captured on CyTOF and analyzed by traditional gating tools and high dimensional data analysis algorithms including Spanning Tree Progression of Density Normalized Events (SPADE).

Results

Figure 10:
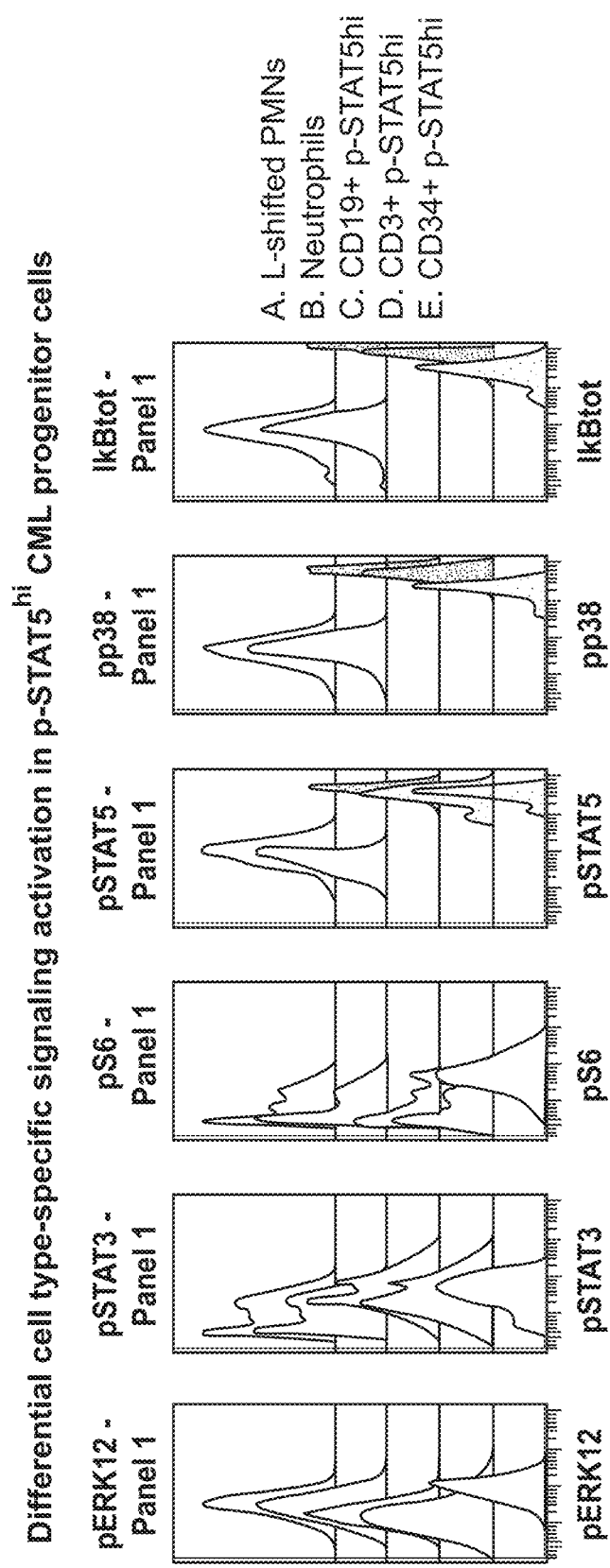
FIG. 10 shows differential cell type-signaling activation in p-STAT$^{hi}$ CML stem/progenitor cells. It illustrates differential STAT5 and p38 MAPK, and IKB kinase activities within the individual p-STAT5$^{hi}$ cell-types as compared to mature neutrophils and immature (L-shifted) neutrophils. Baseline p-STAT5 was low in mature neutrophils compared to L-shifted neutrophils suggesting loss of p-STAT5 as the myeloid lineage cells undergo final maturation and apoptosis. The p-STAT5$^{hi}$ myeloid progenitor/stem cells had lower p38 MAPK and IKB kinase compared to the p-STAT5$^{hi}$ lymphoid progenitor cells.
Figure 11:
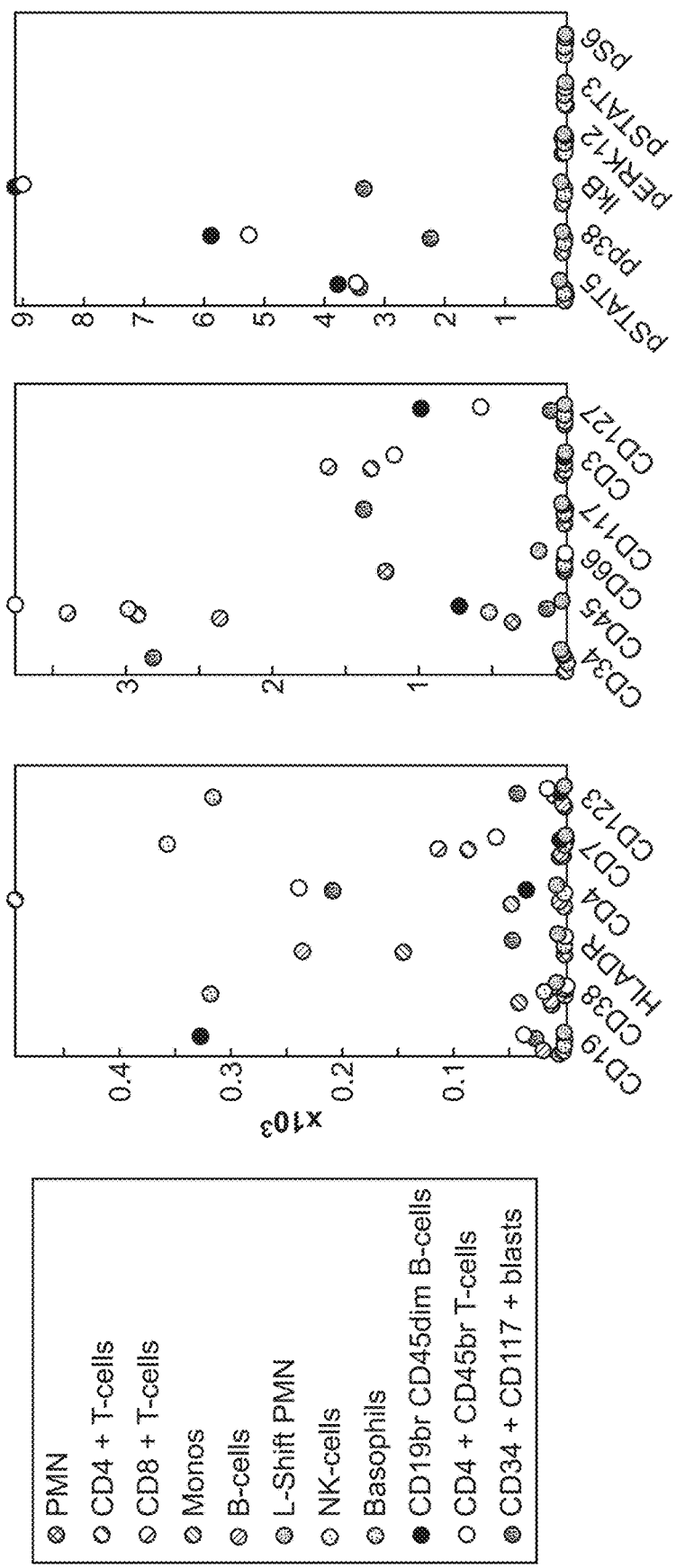
FIG. 11 shows a high dimensional data plot capturing select antigen expression profile in individual cell types displayed with relative cell frequencies. Cells with high IC activities included CD19+/CD45$^{lo}$/IL7R$^{hi}$ and CD3+/CD45+/IL-7R$^{lo}$ lymphoid progenitors and less frequent CD34+/CD117+/IL7R−/IL3R$^{lo}$ myeloid progenitor/stem cells.
Figure 12:
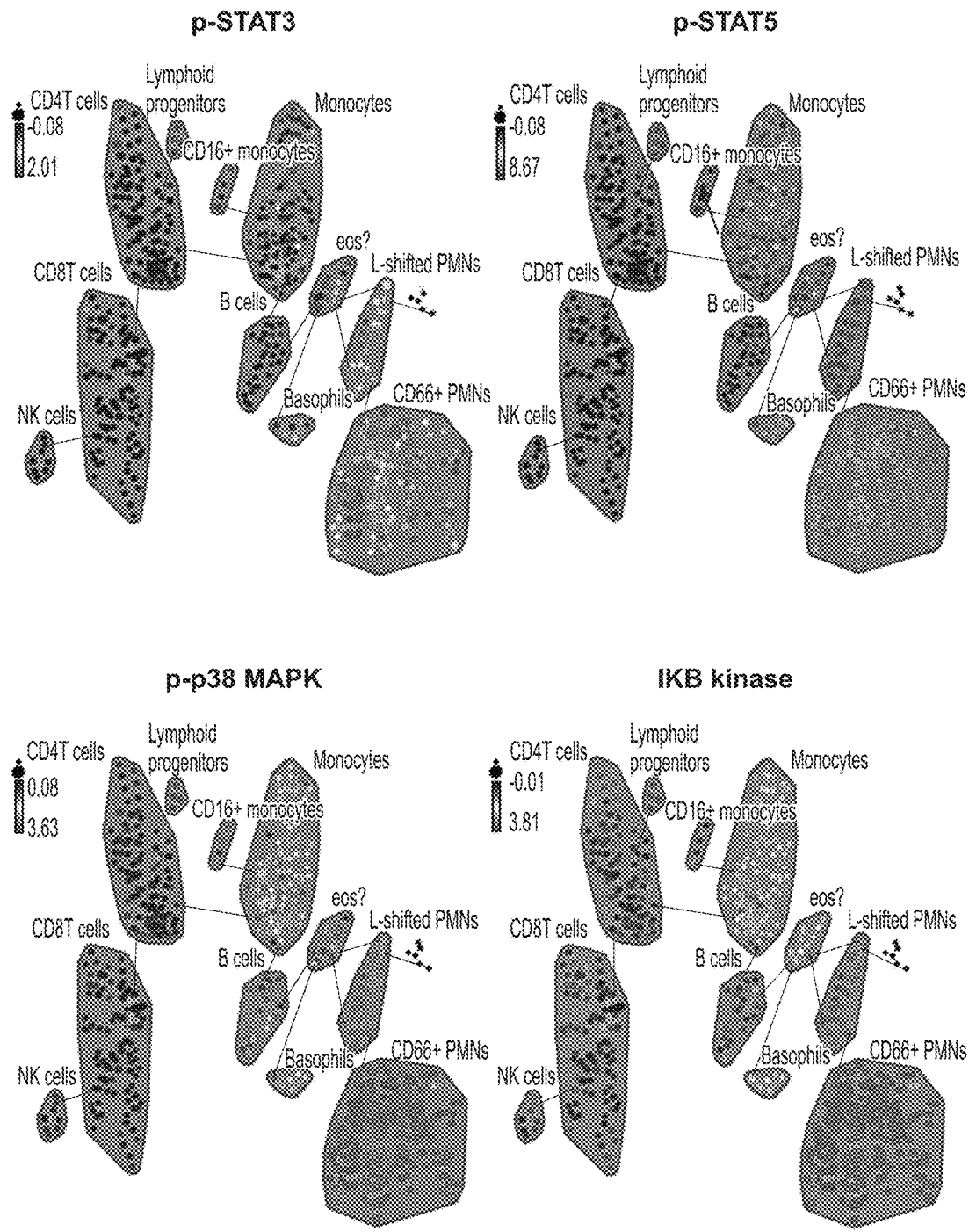
FIG. 12 illustrates mass cytometry data in high dimensional SPADE views to capture expression level of selected readouts in all cells of whole blood with relapsed CML. It illustrates high baseline p-STAT5 activity in lymphoid correlated with p-STAT3 and p-38 MAPK activities and total IKB levels.
Figure 13:
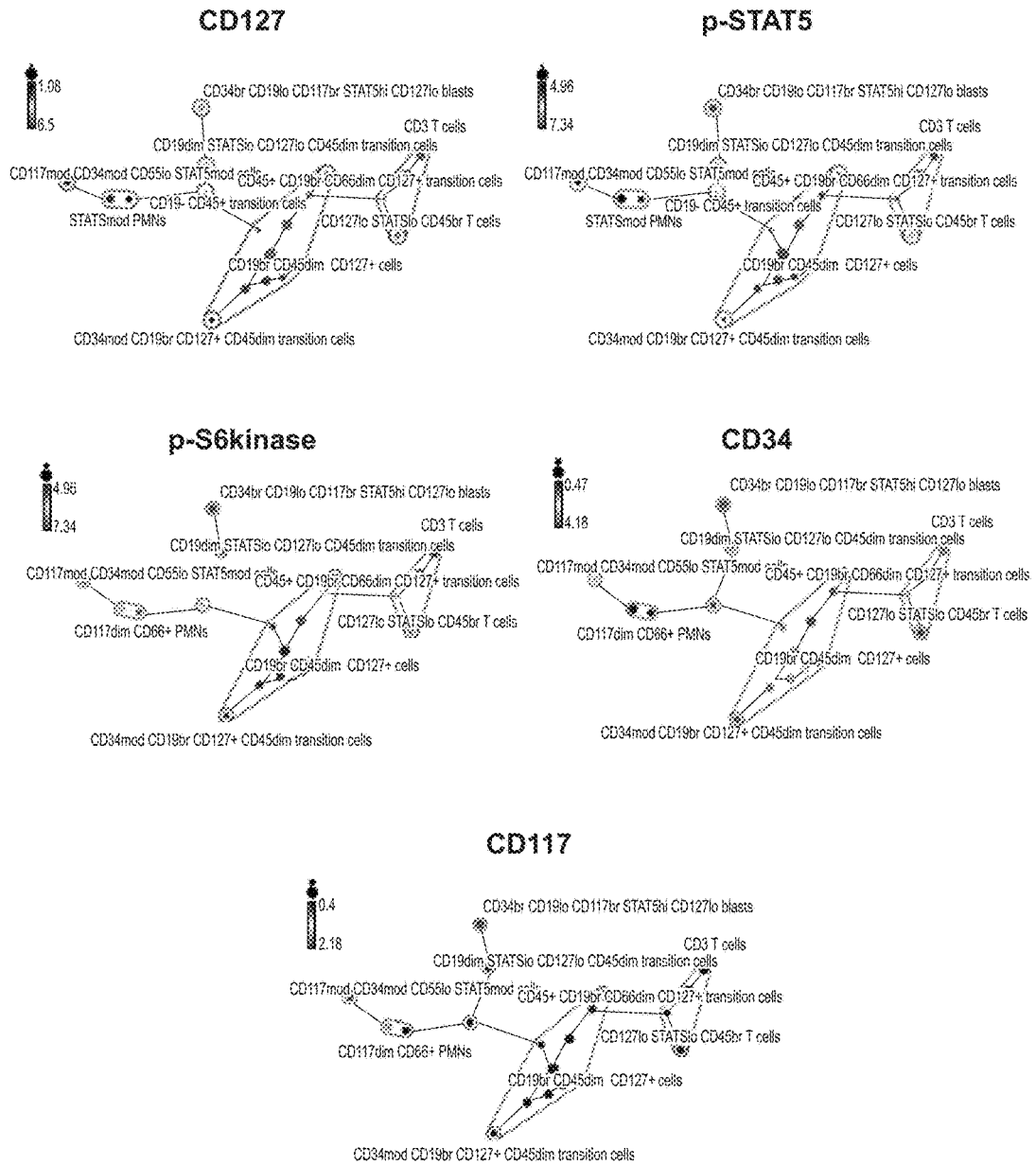
FIG. 13 SPADE analysis view of p-STAT5$^{hi}$ subpopulations shows the CD127$^{lo}$ stem/progenitor cells had relatively high pS6 kinase activity suggestive of mTOR activation.

In CML relapse due to non-adherence, the following observations were made:

By using CD45 and p-STAT5 bivariate plot, clusters of p-STAT$^{hi}$ cells were identified. Further bivariate gating revealed two minor lymphoid subpopulations—CD19+/CD20−/IgD−/CD66−/CD34$^{lo}$/CD45$^{lo}$ progenitor cells (0.36%) and CD3+/CD4+/CD45+ T lymphocytes (0.24%)—with markedly high basal STAT5 and p38 activity that correlated with IL7R/CD127 expression such that IL7R−mature lymphocytes lacked high STAT5 or p38 MAPK activity levels (FIGS. 9-12). A minute myeloid blast population (p-STAT5$^{hi}$/IL3R+/IL7R$^{lo}$/CD34+/CD117+, 0.06%) was detected, with 2× lower p-38 MAPK activity and 3× lower IKB compared to the p-STAT5$^{hi}$/IL-7R+ lymphoid progenitors (FIG. 10 and FIG. 13). The data suggest a role of IL-7R in receptor-mediated p-STAT5 and p-38 MAPK activation, with IL7R+/pSTAT5$^{hi}$/p38MAPK$^{hi}$ lymphoid cells and IL3R+/pSTAT5$^{hi}$/CD34+/CD117+ myeloid cells as potential cell-based biomarkers of relapsed CML and other myeloid neoplasms. Further, CD19+/IL7R+/pSTAT5$^{hi}$/ p38MAPK$^{hi}$ lymphoid cells are likely BCR-ABL(+) and could represent a biomarker for residual/relapsed disease in Ph+ leukemias (including Ph+ B-ALL and biphenotypic leukemia) or early detection of B-lymphoid blast crisis of CML. Additionally, the ratio of CD19+/pSTAT5$^{hi}$/ p38MAPK$^{hi}$ and CD3+/pSTAT5$^{hi}$/p38MAPK$^{hi}$ cells identified with this approach could have prognostic relevance.

IL3R helps distinguish the myeloid stem/progenitor cells in myeloid neoplasms (MPN, AML, MDS, myelodysplastic/ myeloproliferative overlap syndromes) from normal physiologic stem/progenitor cells, and here elevated pS6 kinase activity suggests constitutive mTOR activation in IL3R+ cells (FIG. 13). In this case, the data provide evidence of relapsed leukemia based on cell type-specific functional activity. Thus, assays based on the above combination of markers are useful in detection of residual or early myeloid neoplasms. The assay can be formulated for single tube high parameter analysis necessitating fewer cells than typical multiparameter flow cytometry assays.

Data visualization algorithms help visualize modifications in select parameters and cell-types due to certain select perturbations, enabling high throughput data analysis and interpretation based on abnormal activation patterns.

Interpretation

Differential response to cytokine activation provided evidence for the role of pro-inflammatory milieu that favors myeloid maturation over lymphoid development in CML. The data provided support for the STAT5 pathway as a potential drug target in myeloid neoplasms including BCR/ABL-positive chronic myelogenous leukemia and BCR/ABL− negative chronic myeloproliferative neoplasms (such as primary myelofibrosis), acute myeloid leukemia; and Ph+ B-lymphoblastic or biphenotypic leukemias. Cytokine responsiveness in stem/progenitor cells is a possible indicator of therapy responsiveness based on their known refractoriness to TM-targeted inhibition and data supporting low cytokine responses.

Cytokine-induced effects on STAT5 activity as measured by the mass cytometry assay can be used as a biomarker for response to STAT inhibition, and could serve as a biomarker for response to inhibition of BCR-ABL, an established drug target upstream of STAT pathways. Given the crucial role of IL6, a gene regulated by BCL6 in CML pathogenesis, the data raised doubt on the efficacy of BCL6 repression.

Detection of rare cells with elevated STAT5 and p38 MAPK activity with possible signaling through IL-7R suggests importance of these survival pathways in CML.

Whether STAT5 activity correlates with BCR/ABL expression in these cells, and potential therapeutic relevance of rare circulating IL-7R+ immature cells remains to be elucidated. Furthermore, high STAT5 activity in a rare IL-7R+ T-cell subset could represent an immune escape mechanism or a survival mechanism maintaining chronicity. Thus, for minimal residual disease detection in a case of a clonal neoplasm such as CML, T lymphoid progenitors with abnormal activity levels can be detected and are of potential prognostic relevance.

Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

I claim:

1. A method for preparation of cells for analysis of biomarkers, comprising:
    (a) contacting a sample that contains a population of cells with at least one modulating substance at a first temperature, thereby producing a modulated cell population, wherein the first temperature is about 37° C.;
    (b) contacting the modulated cell population with at least one antibody that is directed to a cell surface biomarker at a second temperature that is lower than the first temperature, thereby producing an extracellularly stained cell population, wherein the second temperature is about 0° C.;
    (c) contacting the extracellularly stained cell population with one or more reagents that fixes and permeabilizes the cells, thereby producing a fixed and permeabilized cell population;
    (d) contacting the fixed and permeabilized cell populations with at least one antibody that is directed to an intracellular biomarker, wherein the biomarker comprises a phosphoprotein and is analyzed in a multiparametric, phos-flow cell analysis;
    wherein the cell population is fixed at about 37° C.

2. A method according to claim 1, wherein the at least one antibody in step (b) is tagged with one or more metal atoms.

3. A method according to claim 1, wherein the at least one antibody in step (d) is tagged with one or more metal atoms.

4. A method according to claim 1, wherein the at least one modulating substance comprises at least one cytokine.

5. A method according to claim 1, wherein the at least one modulating substance comprises IL3, IL6, and/or IFNa2.

6. A method according to claim 1, wherein the multiparametric cell analysis method comprises mass cytometry.

7. A method according to claim 1, wherein the at least one antibody in step (b) is directed to a biomarker selected from a lineage-determining antigen, an activation- and maturation-associated antigen, and a cytokine receptor.

8. A method according to claim 1, wherein the at least one antibody in step (b) is directed to a biomarker selected from CD8a-144Nd, CD4-145Nd, CD20-147Sm, CD16-Nd148, CD45-154Sm, CD11c-159Tb, CD14-160Gd, CD33-166Er, CD24-168Er, CD3-170Er, CD66-171Yb, CD56-175Lu, CD27-152Sm, CD45RA-153Eu, IgD-161Dy, CD38-167Er, HLA-DR-174Yb, CD25-176Yb, IL3R/CD123-151Eu, and IL7R/CD127-158Gd.

9. A method according to claim 1, wherein the at least one antibody in step (b) is a panel of antibodies directed to CD8a-144Nd, CD4-145Nd, CD20-147Sm, CD16-Nd148, CD45-154Sm, CD11c-159Tb, CD14-160Gd, CD33-166Er, CD24-168Er, CD3-170Er, CD66-171Yb, CD56-175Lu, CD27-152Sm, CD45RA-153Eu, IgD-161Dy, CD38-167Er, HLA-DR-174Yb, CD25-176Yb, IL3R/CD123-151Eu, and IL7R/CD127-158Gd.

10. A method according to claim 8, wherein the at least one antibody comprises a metal tag.

11. A method according to claim 9, wherein each antibody in the panel of antibodies comprises a different metal tag.

12. A method according to claim 1, wherein the at least one antibody in step (d) is directed to a biomarker selected from pp38 MAPK-157Gd, total IKB-163Dy, pSTAT3-164Dy, pSTAT1-169Tm, pSTAT5-172Yb, and pPLCy2-173Yb.

13. A method according to claim 1, wherein the at least one antibody in step (d) is a panel of antibodies directed to: pp38 MAPK-157Gd, total IKB-163Dy, pSTAT3-164Dy, pSTAT1-169Tm, pSTAT5-172Yb, and pPLCy2-173Yb.

14. A method according to claim 12, wherein the at least one antibody comprises a metal tag.

15. A method according to claim 13, wherein each antibody in the panel of antibodies comprises a different metal tag.

16. A method according to claim 1, wherein a comprehensive biomarker response profile is generated for cell-specific effects caused by the modulating substance.

17. A method according to claim 1, wherein cells with high biomarker signaling activities are identified to predict the cause of disease relapse, to guide disease therapy, and/or to predict disease outcome.

18. A method according to claim 1, wherein the sample that contains a population of cells comprises a cell line, fresh or frozen mononuclear cells, a fresh human sample, a pathologic sample, or a tissue sample selected from blood, marrow, fine needle aspirate, and a tissue biopsy sample.

19. A method according to claim 1, wherein simultaneous assessment of baseline signaling activities and cell identification is performed.

20. A method according to claim 1, wherein the sample containing a population of cells is not contacted with the modulating substance as in step (a), thereby obtaining a baseline signaling for the sample.

* * * * *